US011554035B2

(12) United States Patent
Sonn

(10) Patent No.: US 11,554,035 B2
(45) Date of Patent: *Jan. 17, 2023

(54) HELIOSTAT TRACKING BASED ON CIRCUMSOLAR RADIANCE MAPS

(71) Applicant: Heliogen Holdings, Inc., Pasadena, CA (US)

(72) Inventor: Alexander Sonn, Pasadena, CA (US)

(73) Assignee: Heliogen Holdings, Inc., Pasadena, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 17/329,959

(22) Filed: May 25, 2021

(65) Prior Publication Data

US 2022/0079790 A1 Mar. 17, 2022

Related U.S. Application Data

(63) Continuation of application No. 16/594,937, filed on Oct. 7, 2019, now Pat. No. 11,017,561.

(Continued)

(51) Int. Cl.
*F24S 50/20* (2018.01)
*F24S 20/20* (2018.01)
(Continued)

(52) U.S. Cl.
CPC ............. *A61F 2/97* (2013.01); *A61F 2/95* (2013.01); *A61F 2/013* (2013.01); *A61F 2/958* (2013.01); *A61F 2002/9511* (2013.01)

(58) Field of Classification Search
CPC .. F24S 20/20; F24S 50/20; F24S 23/00; F24S 23/10; F24S 23/11; F24S 23/12;
(Continued)

(56) References Cited

U.S. PATENT DOCUMENTS 7,906,750 B2 * 3/2011 Hickerson ............. G01S 3/7803
250/203.1
9,010,317 B1 * 4/2015 Gross .................... G01S 3/7861
353/3
(Continued)

FOREIGN PATENT DOCUMENTS

| CN | 103500277 A | * | 1/2014 | |
| WO | WO-2012125748 A2 | * | 9/2012 | ................ F24J 2/07 |
| WO | WO-2017064339 A1 | * | 4/2017 | .............. F24S 50/20 |

OTHER PUBLICATIONS

Freeman et al. "Closed Loop Control System for a Heliostat Field" 2015 IEEE, 6 Pages.*

*Primary Examiner* — Nathnael Aynalem
(74) *Attorney, Agent, or Firm* — Knobbe, Martens, Olson & Bear LLP

(57) ABSTRACT

A system and method for tracking the sun with a heliostat mirror is disclosed. The solar tracking system comprises: a camera configured to capture high dynamic range images of the sky, a plurality of cameras configured to capture images of the heliostat mirror, and a tracking controller. The images of the heliostat mirror include reflections of the sky. The tracking controller is configured to generate a circumsolar radiance map characterizing the brightness of at least a portion of the sky with the high dynamic range images. During tracking operations, the tracking controller is configured to estimate an orientation of the heliostat mirror; calculate coordinates of the portions of sky in the reflections in the heliostat mirror; estimate brightness levels of portions of sky in the reflections of the heliostat mirror based on the calculated coordinates and the radiance model; determine brightness levels of portions of sky in the reflections of the heliostat mirror based on the images from the plurality of cameras; generate an error measurement characterizing a difference between the brightness level estimated from the (Continued)

radiance model and the brightness level determined from the images of the heliostat mirror; search for an orientation angle of the at least one mirror that minimizes the error measurement; and re-orient the at least one mirror based on the orientation angle that minimizes the error measurement.

19 Claims, 8 Drawing Sheets

Related U.S. Application Data

(60) Provisional application No. 62/743,349, filed on Oct. 9, 2018.

(51) Int. Cl.
  *F24S 20/25* (2018.01)
  *A61F 2/97* (2013.01)
  *A61F 2/95* (2013.01)
  *A61F 2/01* (2006.01)
  *A61F 2/958* (2013.01)

(58) Field of Classification Search
  CPC .. F24S 23/70; F24S 23/71; F24S 23/72; F24S 23/82; F24S 25/00; F24S 2030/10; F24S 2030/11; F24S 2030/115; F24S 2030/12; F24S 30/20; F24S 30/40; F24S 30/42; F24S 30/422; F24S 30/428; F24S 30/45; F24S 30/452; F24S 30/455; F24S 30/458; F24S 30/48; F24S 50/00; F24S 50/80; G06T 2207/30181; G06T 2207/30184; G06T 7/70; G06T 7/75; G06V 10/60; H04N 5/247; H04N 7/181; Y02E 10/47; Y02E 10/52; Y02E 10/50
  USPC .................................................. 126/573
  See application file for complete search history.

(56) References Cited

U.S. PATENT DOCUMENTS

| | | | |
|---|---|---|---|
| 9,103,719 B1* | 8/2015 | Ho | G01J 1/1626 |
| 9,482,583 B1* | 11/2016 | Zavodny | G01M 11/005 |
| 9,575,480 B1* | 2/2017 | Azarchs | F24S 50/00 |
| 9,766,122 B2* | 9/2017 | Cothuru | B64C 19/00 |
| 10,359,215 B2* | 7/2019 | Baker | F24S 50/20 |
| 2008/0236568 A1* | 10/2008 | Hickerson | F24S 30/452 |
| | | | 126/578 |
| 2009/0229264 A1* | 9/2009 | Gilon | F03G 6/005 |
| | | | 126/573 |
| 2010/0224232 A1* | 9/2010 | Cummings | F24S 23/74 |
| | | | 136/246 |
| 2011/0120448 A1* | 5/2011 | Fitch | F24S 50/00 |
| | | | 126/601 |
| 2012/0174909 A1* | 7/2012 | Koningstein | F24S 50/20 |
| | | | 126/714 |
| 2012/0193512 A1 | 8/2012 | Wu et al. | |
| 2013/0021471 A1* | 1/2013 | Waterhouse | F24S 50/20 |
| | | | 382/106 |
| 2014/0083413 A1* | 3/2014 | Bibi | F24S 50/00 |
| | | | 702/3 |
| 2017/0198942 A1* | 7/2017 | Baker | H04N 5/247 |
| 2018/0017288 A1 | 1/2018 | Abdel-Hady et al. | |
| 2018/0347879 A1 | 12/2018 | Tada et al. | |
| 2019/0158011 A1* | 5/2019 | West | G06N 20/20 |

* cited by examiner

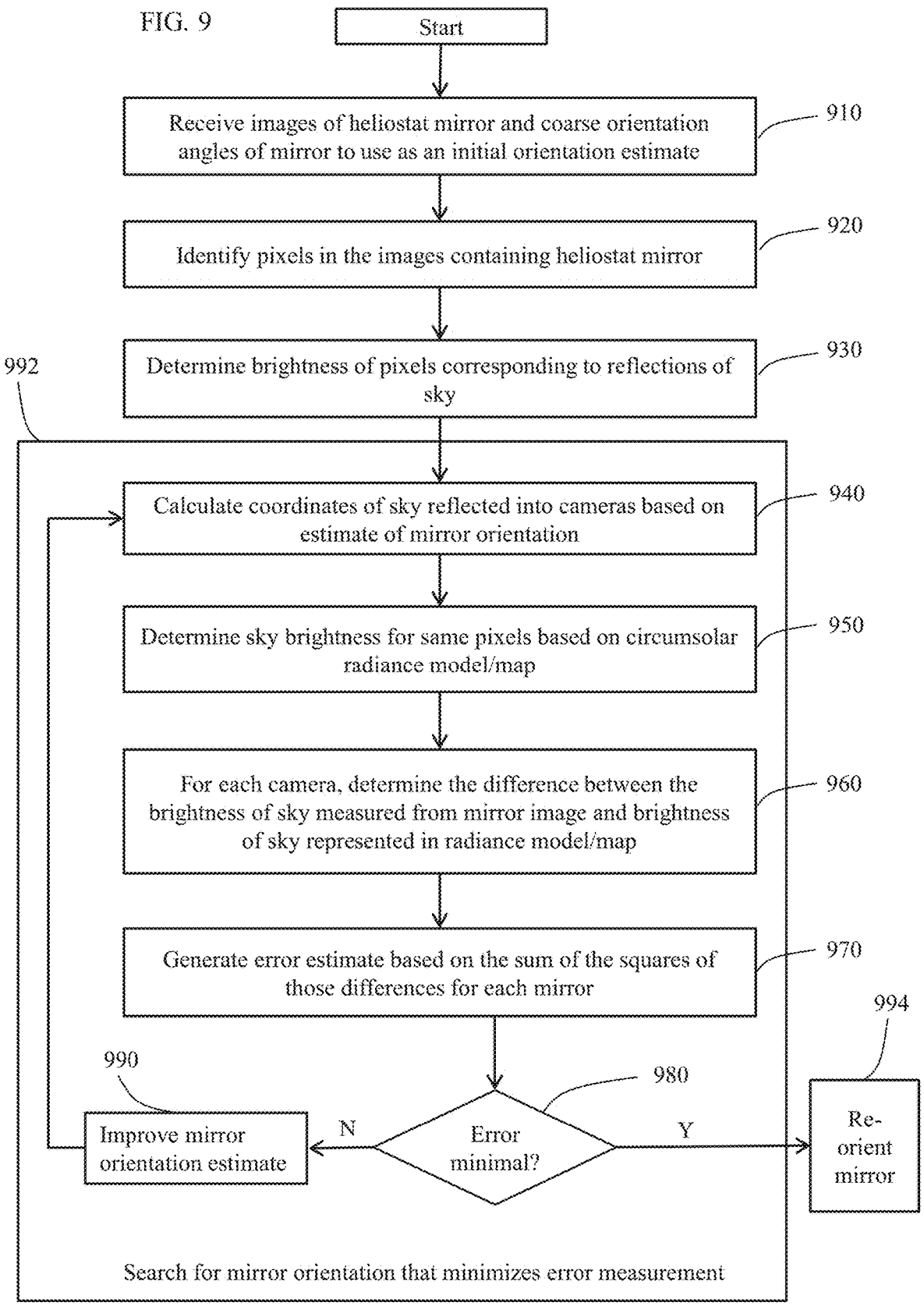

HELIOSTAT TRACKING BASED ON CIRCUMSOLAR RADIANCE MAPS

CROSS-REFERENCE TO RELATED APPLICATION(S)

This is a continuation application of application Ser. No. 11/017,561, filed Oct. 7, 2019, which claims the benefit of U.S. Provisional Patent Application Ser. No. 62/743,349 filed Oct. 9, 2018, titled "Heliostat tracking based on radiance maps," which are hereby incorporated by reference herein for all purposes.

TECHNICAL FIELD

The invention generally relates to a tracking technique for tracking the sun with a heliostat. In particular, the invention relates to a system and method of tracking the sun based on a map of brightness across the sky.

BACKGROUND

The prior art describes a wide range of solar tracking systems for reflecting sunlight to a power tower in a solar thermal plant. The tracking systems are configured to precisely reflect sunlight to a fixed target area of approximately one or two square meters on the power tower's receiver. Sunlight projected onto this receiver is then converted to heat and that heat used to generate electricity, for example.

A key metric for solar thermal plant efficiency is spillage, i.e., how much of the light reflected towards the receiver by the mirrors falls outside target area and is therefore wasted. Multiple factors contribute to spillage, one of which being the accuracy with which heliostat mirrors are oriented to reflect the sun. This mirror aiming accuracy is represented in terms of a "pointing error." Numerous factors contribute to the pointing error including the control systems that command heliostats to move to track the sun. These control systems typically operate in an "open-loop" manner in which a mathematical model of the heliostat drive—represented in terms of kinematic equations—is used to determine how to move the heliostat to reflect the sunlight to the target. An open-loop control system, however, has no feedback guiding or controlling the orientation while the heliostat is aiming sunlight at the receiver. If the model representing the position and orientation of the mirrors is inaccurate, the aim will therefore also be inaccurate.

In the alternative to "open loop" control systems, "closed-loop" control systems use sensory feedback to measure heliostat orientation. There is therefore a need for a sensory feedback mechanism configured to correct the mathematical model of the heliostat drive, thereby reducing the pointing error and reducing spillage.

SUMMARY

The invention features a novel system and method for tracking the sun with a heliostat mirror. In one embodiment, the solar tracking system comprises: a camera configured to capture high dynamic range images of the sky, a plurality of cameras configured to capture images of the heliostat mirror, and a tracking controller. The images of the heliostat mirror include reflections of the sky. The tracking controller is configured to generate a radiance model characterizing the brightness of at least a portion of the sky with the high dynamic range images. During tracking operations, the tracking controller is configured to estimate an orientation of the heliostat mirror; calculate coordinates of the portions of sky in the reflections in the heliostat mirror; estimate brightness levels of portions of sky in the reflections of the heliostat mirror based on the calculated coordinates and the radiance model; determine brightness levels of portions of sky in the reflections of the heliostat mirror based on the images from the plurality of cameras; generate an error measurement characterizing a difference between the brightness level estimated from the radiance model and the brightness level determined from the images of the heliostat mirror; search for an orientation angle of the at least one mirror that minimizes the error measurement; and re-orient the at least one mirror based on the orientation angle that minimizes the error measurement.

The plurality of cameras configured to capture images of the heliostat mirror include at least three and preferably four cameras. The four cameras comprise a first camera above the receiver aperture, a second camera below the receiver aperture, a third camera to the left of the receiver aperture, and a fourth camera to the right of the receiver aperture. The search for the orientation angle of the at least one mirror that minimizes the error measurement comprises searching for the orientation angle of the at least one mirror that minimizes the error measurement using a Nelder-Mead search algorithm.

The method of tracking the sun with a heliostat mirror, receiver, and plurality of cameras comprises: generating a radiance model characterizing the brightness of at least a portion of the sky; estimating an orientation of the heliostat mirror; calculating coordinates of portions of sky in reflections of the heliostat mirror; estimating brightness levels of the portions of sky in reflections of the mirror based on the calculated coordinates and the radiance model; determining brightness levels of the portion of sky in the reflections in the mirror based on the images of the mirror; generating an error measurement characterizing a difference between the brightness level estimated from the radiance model and the brightness level determined from the images of the mirror; searching for an orientation angle of the mirror that minimizes the error measurement; and re-orienting the heliostat mirror based on the orientation angle that minimizes the error measurement.

BRIEF DESCRIPTION OF THE DRAWINGS

The present invention is illustrated by way of example and not limitation in the figures of the accompanying drawings, and in which:

FIG. 9 is a flowchart of the process of determining a mirror orientation using the circumsolar radiance model, in accordance with the preferred embodiment of the present invention.

DETAILED DESCRIPTION OF THE PREFERRED EMBODIMENT

Figure 1:
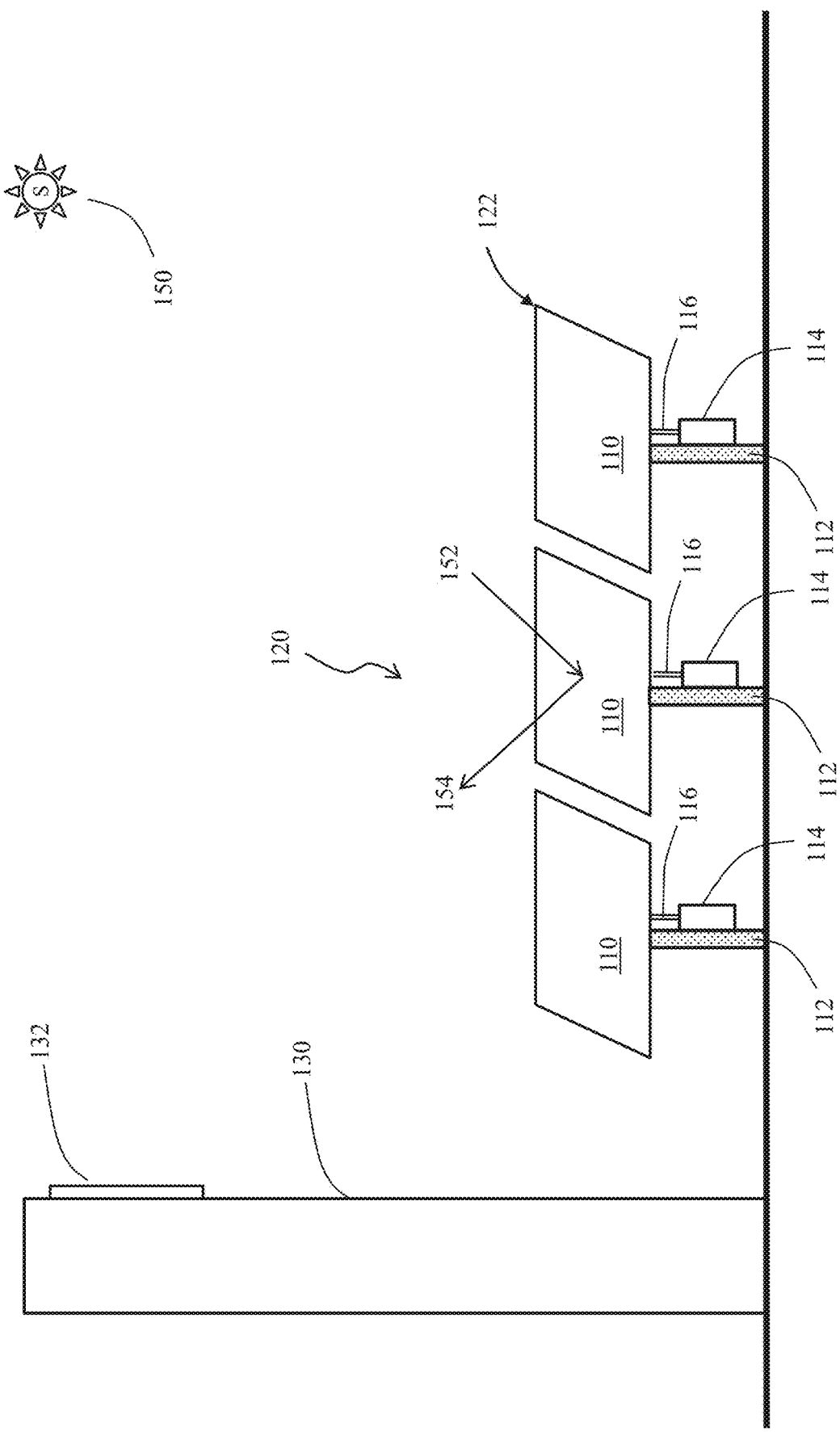
FIG. 1 is an elevation view of an array of heliostats and a solar thermal receiver, in accordance with the preferred embodiment of the present invention.

The present invention pertains to a solar tracking system implemented with an array of heliostats and a solar thermal receiver that captures energy reflected from the heliostat array. Illustrated in FIG. 1 is an elevation view of heliostat array 120 and receiver 130 in accordance with a preferred embodiment. The heliostat array includes numerous identical heliostats 122 that are distributed in two dimensions in proximity to the receiver. Each heliostat 122 includes a mirror 110 pivotably coupled to a frame or stanchion 112 affixed to the ground and/or other heliostats. Each heliostat further includes a circumsolar tracking controller 114 configured to determine the proper orientation of one or more mirrors through the day. A mirror is properly oriented when the incoming light 152 from the sun 150 is reflected to the solar thermal receiver 130, specifically the receiver aperture 132. If the actual orientation of the mirror differs from the proper orientation at that instant, the tracking controller energizes actuators 116 that drive the mirror to the proper orientation.

Figure 2:
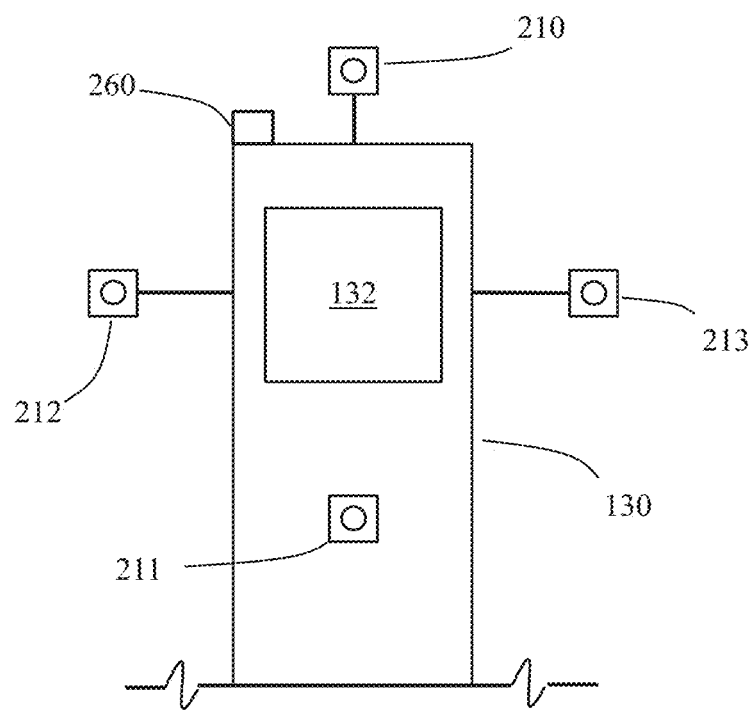
FIG. 2 is a front side view of the solar thermal receiver, in accordance with the preferred embodiment of the present invention.

Illustrated in FIG. 2 is an elevation view of the front side of the solar thermal receiver 130 and aperture 132 that admits sunlight into the receiver. The receiver 130 may further include absorbers and heat exchangers (not shown) that convert the sunlight to heat and transfer the heat to air, water, molten salt, or other working fluid. In the preferred embodiment, the receiver 130 has mounted to it a portion of the solar tracking system, namely three or more cameras 210-213 configured to capture images of the heliostat mirrors 120 and the reflections of the sky therein. In this particular embodiment, the three or more cameras includes the upper camera 210, lower camera 211, left camera 212, and right camera 213, which are all the same distance from the aperture. The cameras 210-213 may be any of a number of different types of two dimensional imagers including still cameras and video cameras.

The cameras 210-213 are configured to capture images of the reflections in the heliostat mirrors. When a heliostat mirror is properly reflecting light to the aperture 132, the reflection observed in each mirror by the cameras 210-213 generally include a segment of sky within a few degrees of the sun. Image data observed by the multiple cameras are combined to determine the orientation angles of each heliostat mirror. In particular, image data from the upper camera 210, lower camera 211, left camera 212, right camera 213 are combined to determine the azimuth angle and elevation angle of each heliostat mirror 110.

The receiver 130 may further include a High Dynamic Range camera 260 configured to acquire a sequence of images of the sun and the region around the sun for purposes of generating a circumsolar radiance map of the sky, which is then used for solar tracking operations.

Figure 3:
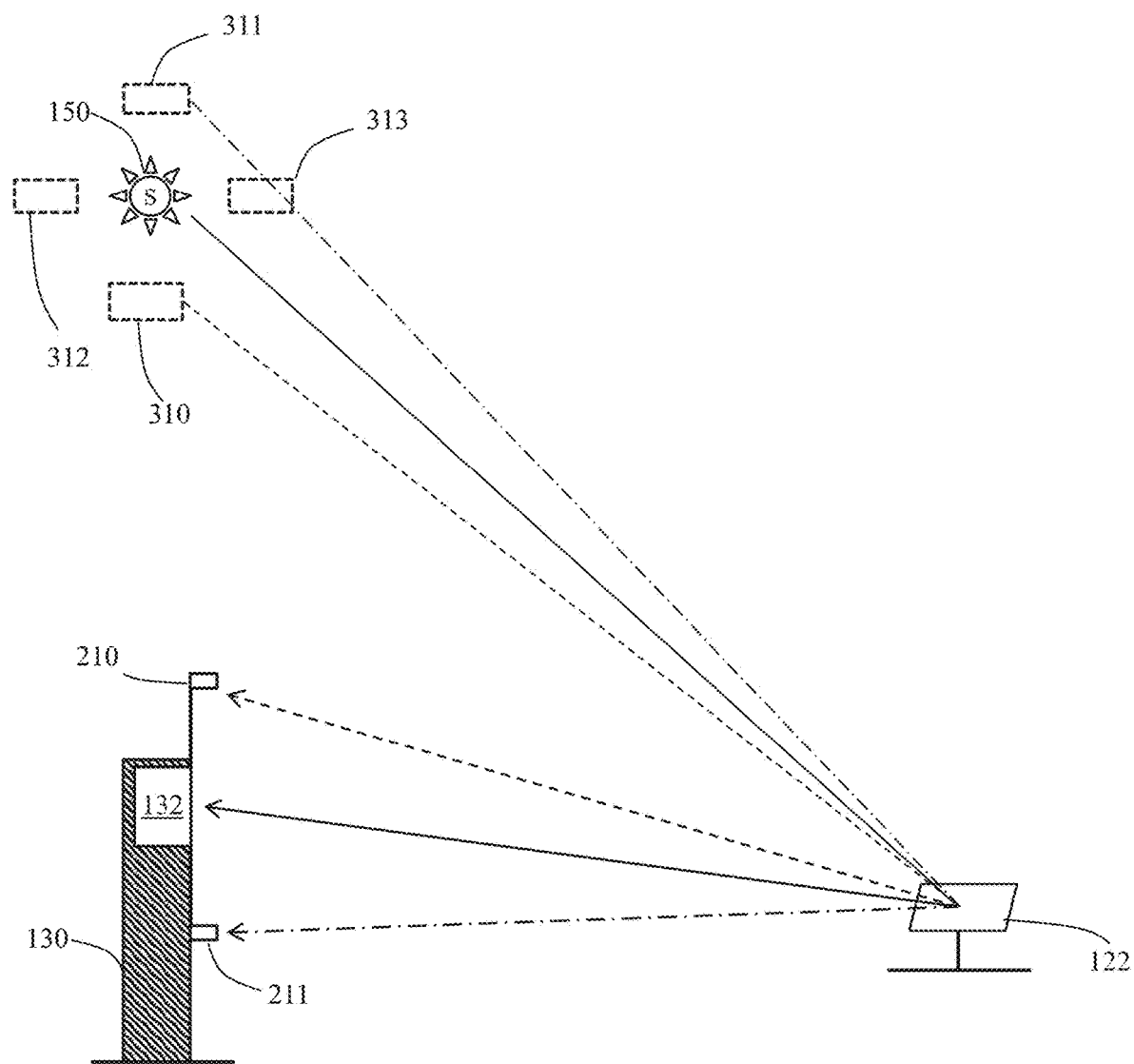
FIG. 3 is a diagrammatic illustration showing regions of sky seen by receiver-mounted cameras through a heliostat mirror, in accordance with the preferred embodiment of the present invention.

Illustrated in FIG. 3 is a cross section of the solar thermal receiver showing the source of light incident on the receiver and cameras 210-211. When the heliostat mirror 122 is properly oriented, the light from the sun 600 is reflected onto or into the receiver aperture 132. At the same time, light is captured by cameras 210, 211. In the preferred embodiment, the distance between the cameras 210, 211 and the aperture is large enough to ensure that the cameras never image the sun in the reflection from the heliostat mirror 122 while tracking. Instead, the upper camera 210 receives a reflection of light that originates from a section 310 of the sky below the sun 150, i.e., a solid angle at a lower elevation angle than the sun. From the same heliostat mirror, the lower camera 211 receives a reflection of light that originates from a section 311 of the sky above the sun 150.

Although not shown in FIG. 3, cameras 212, 213 also observe reflections of light that originate from sections 312, 313 of the sky, respectively. The left camera 212 receives a reflection of light that originates from a section of the sky to the right of the sun 150, while the right camera 213 receives a reflection of light that originates from a section of the sky to the left of the sun 150 for the same heliostat mirror.

Figure 4:
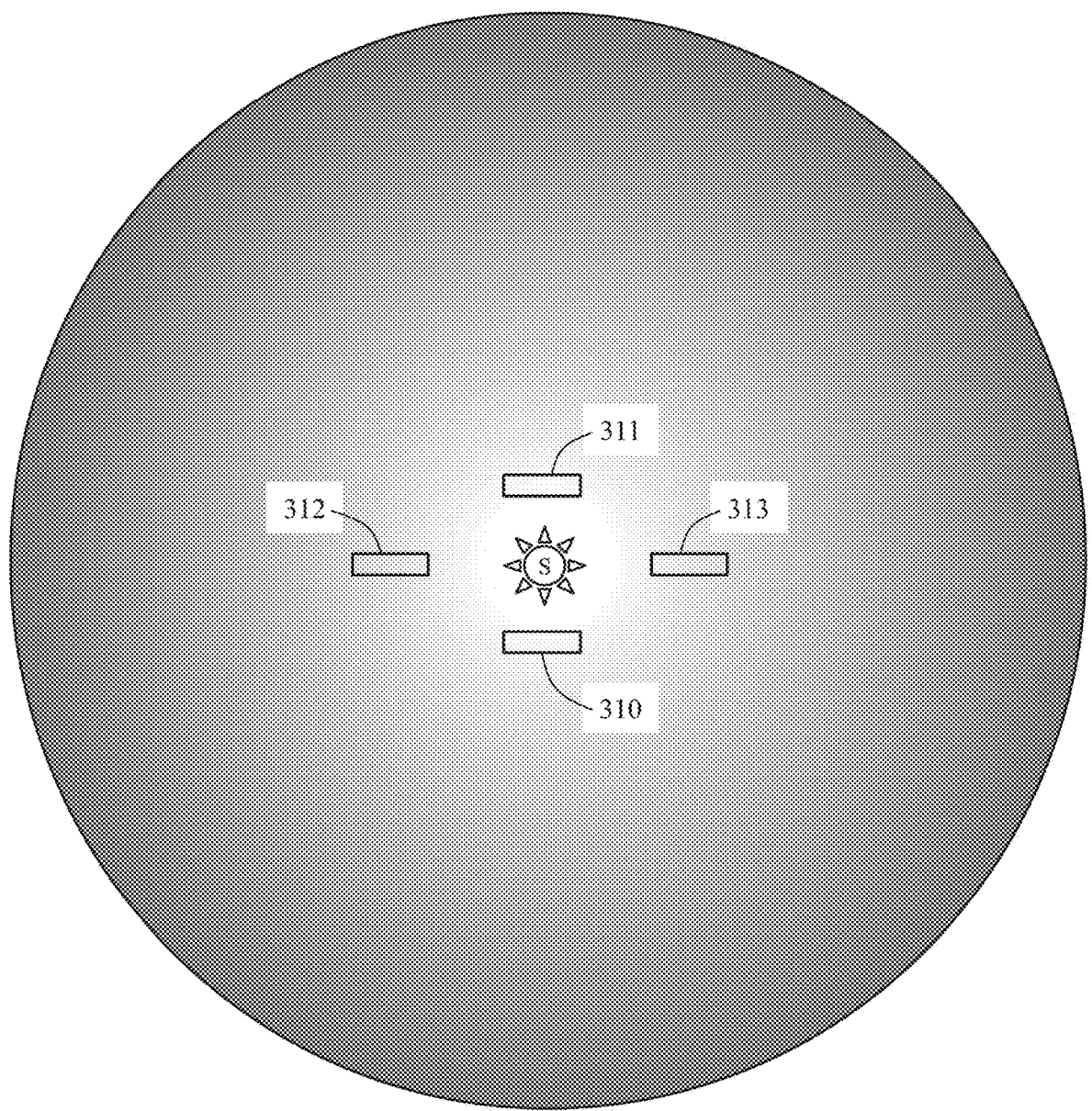
FIG. 4 is a radiance map showing regions of sky seen by receiver-mounted cameras through a heliostat mirror, in accordance with the preferred embodiment of the present invention.

The area of the sky around the sun generally produces some non-zero light pattern since the atmosphere scatters sunlight. This pattern of light is depicted in the circumsolar radiance map in FIG. 4. As shown, the region close to the sun is generally relatively bright while the region of sky furthest from the sun is relatively dark. For a particular mirror, the present invention measures the intensity of the sky at region 310 at camera 210, region 311 at camera 211, region 312 at camera 212, and region 313 at camera 213. Based on the observed intensities, the tracking controller determines the orientation of the associated mirror 110 and how to adjust the mirror, if necessary, to direct sunlight to the receiver aperture 132.

Figure 5:
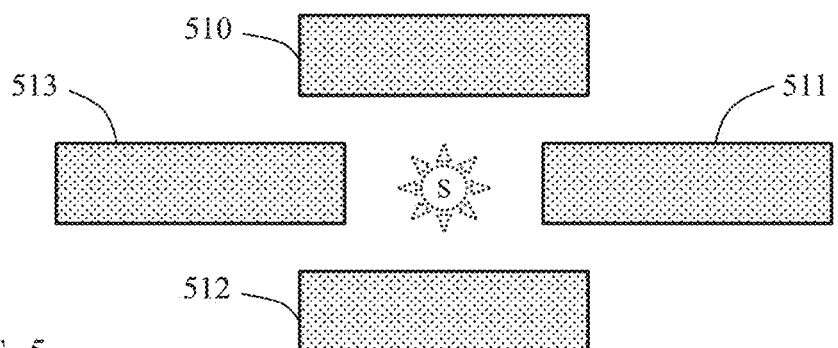
FIG. 5 shows circumsolar radiance as seen by receiver-mounted cameras in a heliostat mirror that is centered on the sun, in accordance with the preferred embodiment of the present invention.

When the images of the reflections of the sky are observed in one heliostat mirror by the four cameras, the portions of sky map to four different angular positions around the sun. The portions of sky visible to the four cameras are illustrated diagrammatically in FIGS. 5 and 6. When the mirror 122 normal vector is properly oriented to reflect light on the aperture 132 and substantially bisects the angle between the top and bottom cameras 210, 211, the intensity of light observed in the upper and lower reflections is roughly the same. Similarly, when the mirror normal vector bisects the angle between the left and right cameras 212, 213, the intensity of light in reflections observed in the mirror by the left and right cameras is roughly the same. This is illustrated in FIG. 5. At a high level of precision, however, the circumsolar radiance is sometimes anisotropic and the intensity of light in reflections not the same even when the mirror normal vector bisects the angle between cameras. The present invention measures this anisotropic light intensity and uses it to improve the accuracy of the tracking operation.

Figure 6:
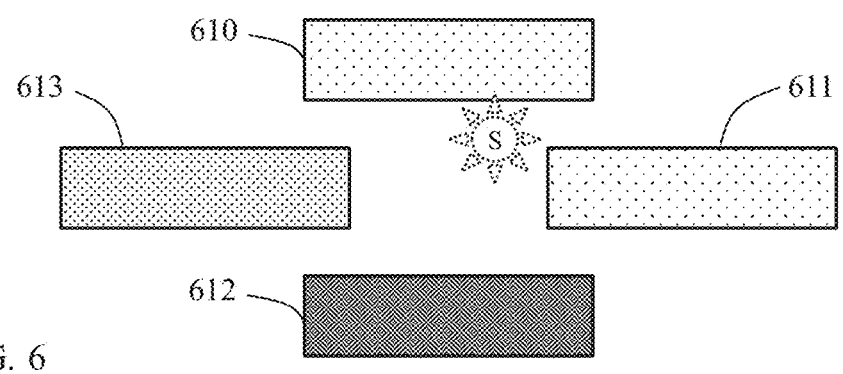
FIG. 6 shows circumsolar radiance as seen by receiver-mounted cameras in a heliostat mirror that is not centered on the sun, in accordance with the preferred embodiment of the present invention.

When the mirror normal is not properly oriented to reflect light on the aperture, however, the normal vector does not bisect the angle between the two cameras and the intensity of light measured in the mirror by opposing cameras (e.g., upper and lower cameras, or left and right cameras) is not the same. This is illustrated in FIG. 6. When the mirror 122 elevation angle of the mirror is off, the reflections of the sky seen by the upper camera and lower camera generally differ. One reflection will appear relatively bright and the other relatively dark. Similarly, when the mirror 122 azimuth angle is off, the reflections of the sky seen by the left camera and right camera will differ with one appearing relatively bright and the other relatively dark.

Figure 7:
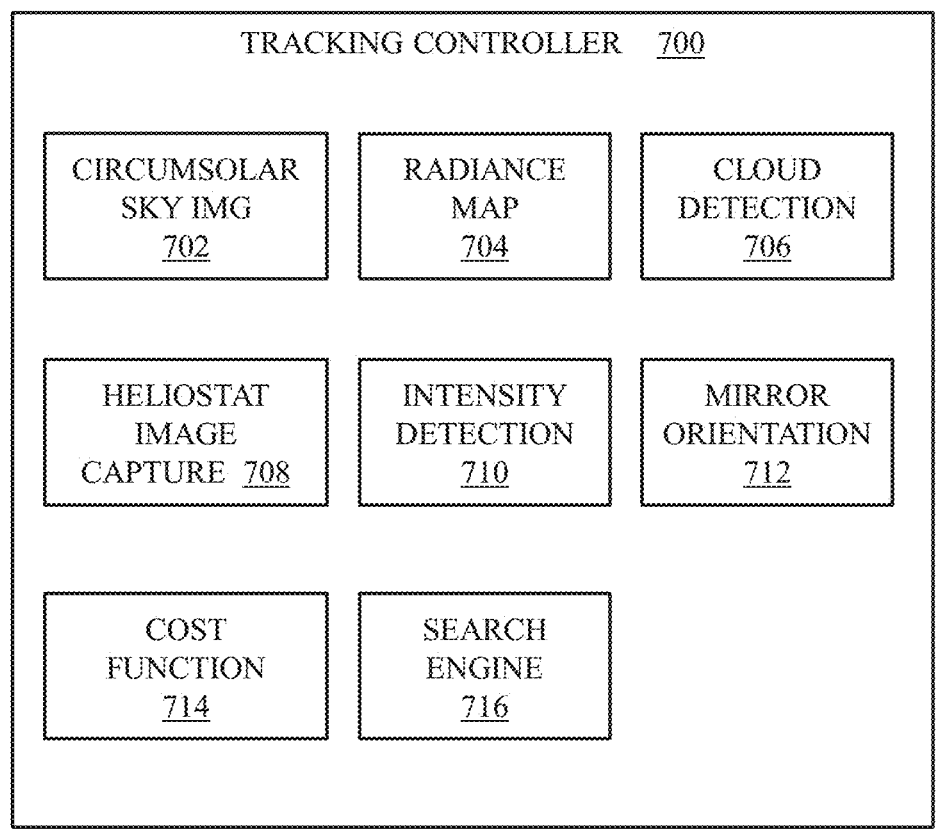
FIG. 7 is a functional block diagram of the circumsolar tracking controller, in accordance with the preferred embodiment of the present invention.

Illustrated in FIG. 7 is a functional block diagram of a circumsolar tracking controller 114 for aiming the mirrors 122 and tracking the sun at each heliostat 120. The tracking controller 114 includes a module for capturing a circumsolar sky image 702, a module for generating a radiance model, i.e., map of the sky 704, a cloud detection module 706, a module for capturing images of heliostats 708, a module for determining an intensity of sky reflections 710, a module for determining mirror orientations 712, a cost function generator 714, a search engine 716, and power supply for energizing actuators 116.

The module for capturing a circumsolar sky image 702 is coupled to the High Dynamic Range camera 260 for capturing one or more images of the sky. In one embodiment, the images of the sky are captured with different exposure times for purposes of measuring the sky brightness over a wide dynamic range. The module for generating a radiance model 704 then uses the images to construct an analytical representation of the intensity of sunlight across the sky, preferably the entire sky for the 2π solid angle. This radiance model 704 then serves as a map of the brightness of the sky for purposes of comparing the image intensities during tracking operations.

During tracking operations, the tracking controller 114 acquires images of the heliostat mirrors, including reflections of the sky, with the image capture module 708. The images are processed by the intensity detection module 710 for purposes of determining the intensity of the reflection of the sky as observed in each mirror by the four cameras 210-213. The intensity detection module 710 may also account for dust on the mirror 122 as well as other factors that can attenuate or alter the light reflected. These intensity measurements may be derived from one pixel in the reflection of the sky, or multiple pixels corresponding to a region of sky visible in the reflection.

Based on the observed intensities, the mirror orientation module 712 determines which section of sky is being observed and the corresponding mirror orientation that would result in that observation. In the preferred embodiment, the section of sky is determined using a search engine 716 that tests multiple possible orientations of the mirror to minimize a cost function 714.

Figure 8:
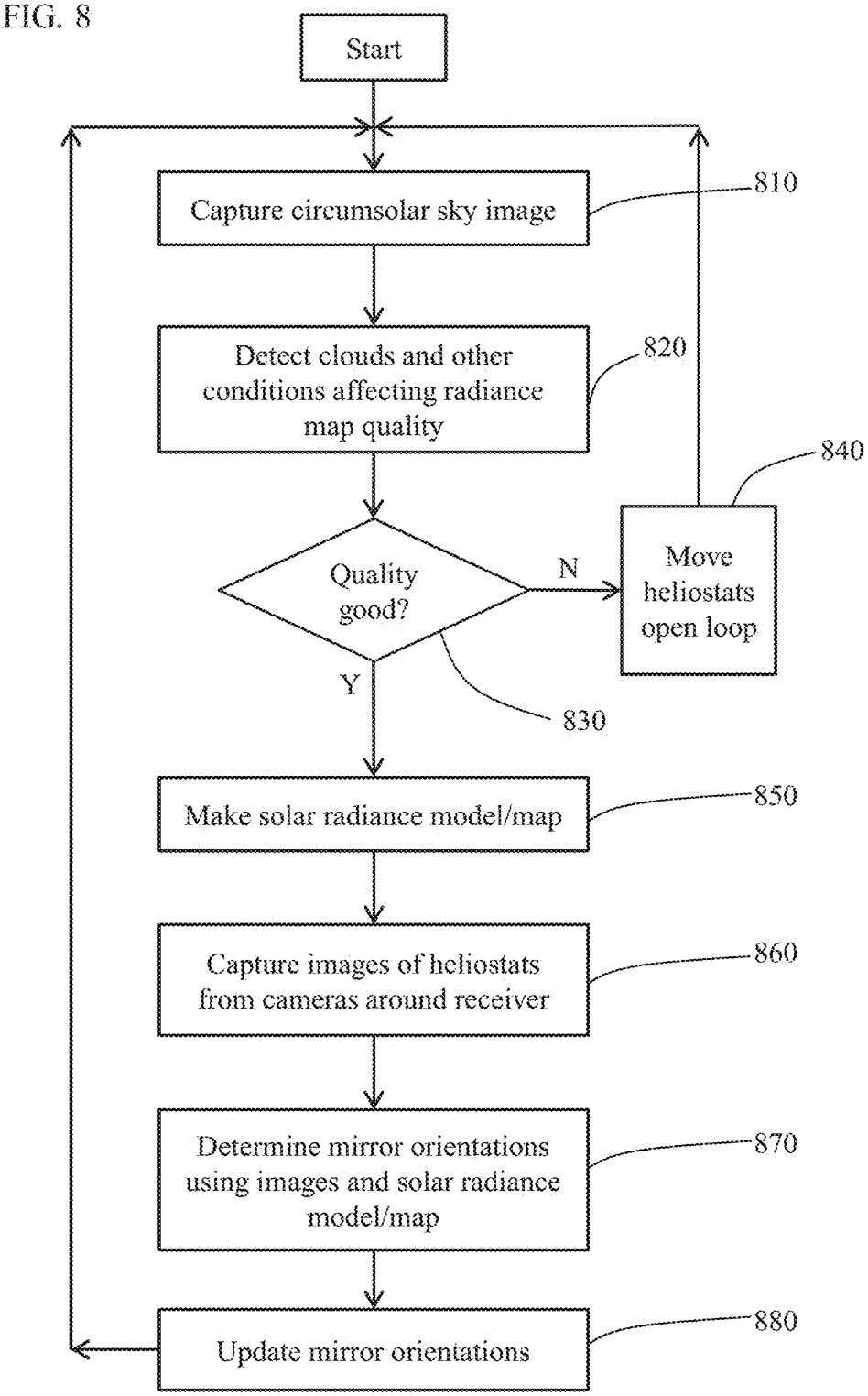
FIG. 8 is a flowchart of the process of tracking the sun using the circumsolar tracking controller to track the sun, in accordance with the preferred embodiment of the present invention.

Illustrated in FIG. 8 is method of tracking the sun using the circumsolar tracking controller 114. To begin, the High Dynamic Range camera 260 acquires 810 a sequence of images of the sun and the region around the sun. These images have increasingly long exposures in order to capture the circumsolar irradiance across a very wide dynamic range. In particular, images are captured at a sequence of exposures, e.g. doubling the exposure for each image. At the shortest exposure, no pixels except perhaps those on the sun itself are saturated. At the longest exposure, the sky at the edge of the image is bright enough to achieve an acceptable signal to noise ratio. These images are used to make a 2-dimensional map of the brightness of the sky around the sun, e.g., using HDR techniques such as those described by P. E. Debevec and J. Malik, "Recovering high dynamic range radiance maps from photographs," in Proceedings of the ACM SIGGRAPH 2008 Classes (SIGGRAPH '08), p. 31, ACM, Los Angeles, Calif., USA, August 2008, which is hereby incorporated by reference herein. In some embodiments, the camera 260 includes an occluding ND filter mounted on an arm in front of the camera such that it is more or less in the center of the image. In operation, the camera is oriented so that the sun is behind the ND filter where it is still visible but much darker, thereby reducing artifacts from the sun.

Preferably, the camera 260 is constructed and oriented in such a way as to minimize undesirable optical effects in the image, including internal reflections, Newton's rings, diffraction spikes, Airy disks and rings, etc. A model of the camera optics providing a mapping between image pixel space and angle space relative to the camera optical axis can be made. A model of the camera vignetting can be made and used to correct images captured from the camera. The camera may be aimed in such a way that the sun is at the optical center of the image, thereby providing a good view of the circumsolar sky (aka sun/solar aureole) and minimizing error caused by internal reflections. As the sun moves over the course of the day, the camera 260 also moves in accordance with some combination of open-loop control and closed-loop/feedback control using images from the camera.

In some embodiments, cloud detection algorithms are also applied 820 to the images from the High Dynamic Range camera 260. The cloud detection effectively determines whether or not it is possible to get reliable results from the mirror orientation solution described below. If clouds or other obstructions prevent the acquisition of a quality image, or if the brightness of a piece of sky reflected by a heliostat into a camera deviates significantly from the expected value, decision block 830 is answered in the negative and affected heliostats are made to track 840 the sun in accordance with an open-loop tracking algorithm. In some embodiments, the cloud detection is used to eliminate areas of the sky with clouds when fitting the parameters of the analytical model of circumsolar radiance using the HDR images.

If the images are clear and free of clouds, for example, decision block 830 is answered in the affirmative and a model or map of the sky, i.e., specifically the circumsolar radiance, generated 850 from the sequence of images from camera 260. In particular, a brightness map is constructed using the images to solve for parameters of a function, e.g., polynomial or exponential, that characterize the image brightness across the sky. The brightness map in the preferred embodiment includes variations in brightness based on the radial distance from the sun as well the anisotropic changes around the circumference of the sun. In the alternative, a map can be constructed by using the image pixels as samples in a 2D interpolant.

In addition to the circumsolar radiance model, the brightness of portions of the sky is determined from images of heliostats acquired 860 with cameras 210-213. Using the brightness measurements from the radiance model and the measure brightness from the images of the heliostats, the circumsolar tracking controller determines 870 the heliostat mirror orientations using the search procedure provided in detail in FIG. 9. Thereafter, the orientations of the mirrors are updated 880 in order to continuously reflect sunlight onto the receiver aperture 132.

Illustrated in FIG. 9 is a method of determining precise mirror orientations using the circumsolar radiance model. To track the sun with a particular mirror, the circumsolar tracking controller receives 910 or retrieves a coarse estimate of the orientation of the mirror as well as images of the mirror from the plurality of cameras 210-213 near the receiver aperture 132. The coarse estimates may be based on the last known orientation of the mirror or the previous tracking operation, for example, or the best guess of the orientation of the mirror.

The circumsolar tracking controller then identifies 920 the portions of the images depicting the mirror. The portion of the image can include one or more pixels from each image. These pixels depict reflections of a particular region of sky based on the orientation of the mirror. The brightness of the pixels is determined 930 as a measure of the circumsolar radiance. When using a plurality of pixels from an image, the brightness of the pixels may be aggregated and represented by a single value such as the median value or mean value, for example.

The same pixels depicting reflections of a particular region of sky, along with the coarse estimate of the mirror orientation, are used to calculate 940 the coordinates of the sky from which the brightness was measured. There are a separate set of sky coordinates for each of the four camera 210-213 image. Using the sky coordinates, the tracking controller 114 determines 950 the brightness of the sky from the radiance model. That is to say, the tracking controller calculates 940 the coordinates of the sky from which each camera 210-213 is seeing a reflected image in the mirror using the known locations of the cameras and mirror and given an orientation of the mirror.

Using the coordinates of the sky from which each camera 210-213 is seeing a reflection in the mirror, the tracking controller 114 determines four brightness estimates (one for each camera 210-213) by 950 looking up the sky coordinates in the radiance model that correspond to what each camera sees in the mirror based on the estimated mirror orientation.

As this point, the tracking controller has four brightness estimates generated from the images of the mirror, and four brightness estimates generated from the circumsolar radiance model (a pair of brightness estimates for each camera). The tracking controller 114 then determines 960 the difference between the brightness of sky measured from a mirror image and brightness of sky represented in the radiance model, for each image of the mirror. An error estimate based on the sum of the squares of those differences is generated 970. The tracking controller actively searches 992 for the orientation angles of the mirror that minimize the error estimate. Until that error is minimized, decision block 980 is answered in the negative and an improved orientation estimate made 990 using the Nelder-Mead technique, for example. Using the new estimate of the orientation angles, the tracking controller, again calculates sky coordinates 940, determines 950 four sky brightness values based on the new sky coordinates, determines 960 differences between measured and calculated sky brightness, and generates 970 an error estimate.

When the error is minimal, decision block 980 is answered in the affirmative and the tracking controller proceeds to re-orient 994 the mirror elevation angles to center the sun on the receiver aperture, as described in step 880 in FIG. 8. If there is more than one heliostat in the camera 210-213 image, the process may be repeated for the mirror on each of the heliostats. Thereafter, the process may be repeated for the next update of the mirror orientation, or for the next mirror 110 in the heliostat array 120.

The error measurement is then minimized in search process 992 using any of a number of search algorithms known to those of skill in the art. The search algorithm effectively searches for the set of mirror orientation angles that produce brightness measures from the radiance model that best match the brightness measurements derived from the mirror images.

In the preferred embodiment, the circumsolar tracking controller 114 implements a nonlinear solving technique such as the Nelder-Mead technique to solve for the orientation of the mirror and a brightness scaling factor, for example. In the Nelder-Mead technique, the error function is computed as follows: (1) take in values for the orientation (azimuth and elevation) of the mirror normal and a brightness scale factor that converts between sky brightness as measured in the circumsolar camera 260 and mirror brightness to account for mirror cleanliness and camera sensitivity, for example; (2) using the known locations of the cameras and mirror and the guessed orientation, calculate the coordinates of the piece of sky each camera sees reflected off of the mirror; (3) compute the brightness for each camera at those calculated coordinates in the 2D brightness map derived from the circumsolar camera images, and scale by the guessed scale factor; and (4) for each camera, take the difference between the measured brightness of the mirror in the image and brightness-map-calculated brightness, and add up the squares of those differences. This is the "error" provided as an output of the error function. Once the mirror normal vectors are determined, the orientations of the heliostat mirrors are updated. This process is repeated sufficiently frequently in order to properly track the sun over the course of the day.

One or more embodiments of the present invention may be implemented with one or more computer readable media, wherein each medium may be configured to include thereon data or computer executable instructions for manipulating data. The computer executable instructions include data structures, objects, programs, routines, or other program modules that may be accessed by a processing system, such as one associated with a general-purpose computer or processor capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. Examples of mass storage devices incorporating computer readable media include hard disk drives, magnetic disk drives, tape drives, optical disk drives, and solid state memory chips, for example. The term processor as used herein refers to a number of processing devices including personal computing devices, servers, general purpose computers, special purpose computers, application-specific integrated circuit (ASIC), and digital/analog circuits with discrete components, for example.

Although the description above contains many specifications, these should not be construed as limiting the scope of the invention but as merely providing illustrations of some of the presently preferred embodiments of this invention.

Therefore, the invention has been disclosed by way of example and not limitation, and reference should be made to the following claims to determine the scope of the present invention.

I claim:

1. A solar tracking system for orienting at least one heliostat mirror, the system comprising:
   a first camera configured to capture at least one image of a sky;

a plurality of cameras mounted in proximity to a receiver, each camera configured to capture an image of the at least one mirror, each image including a reflection of a portion of the sky in the at least one mirror; and
a tracking controller configured to:
  a) generate a model of the sky from the at least one image captured by the first camera, the model characterizing a light level of at least a portion of the sky;
  b) for each camera mounted in proximity to the receiver, calculate coordinates of a portion of sky in a reflection of the at least one mirror;
  c) for each camera mounted in proximity to the receiver, estimate a light level of a portion of sky in a reflection of the at least one mirror based on the calculated coordinates and the model;
  d) for each camera mounted in proximity to the receiver, determine a light level of the portion of sky in the reflection of the at least one mirror based on the images from the plurality of cameras;
  e) generate an error measurement characterizing a difference between the light level estimated from the model and the light level determined from the images of the at least one mirror;
  f) search for an orientation angle of the at least one mirror that minimizes the error measurement; and
  g) re-orient the at least one mirror based on the orientation angle that minimizes the error measurement.

2. The solar tracking system of claim 1, wherein the determined light level is determined from one or more pixels associated with the portion of sky in the reflection of the at least one mirror visible in the images captured by the plurality of cameras mounted in proximity to the receiver.

3. The solar tracking system of claim 2, wherein the light level is determined based on an average or median brightness associated with the one or more pixels.

4. The solar tracking system of claim 3, wherein the coordinates of the portion of sky in the reflection of the at least one mirror are calculated based on said one or more pixels.

5. The solar tracking system of claim 4, wherein the plurality of cameras mounted in proximity to the receiver are mounted within ten meters of the receiver.

6. The solar tracking system of claim 5, wherein the plurality of cameras mounted in proximity to the receiver are mounted within ten meters of a receiver aperture.

7. The solar tracking system of claim 6, wherein the plurality of cameras comprise four cameras.

8. The solar tracking system of claim 7, wherein the four cameras comprise a first camera above the receiver aperture, a second camera below the receiver aperture, a third camera to the left of the receiver aperture, and a fourth camera to the right of the receiver aperture.

9. The solar tracking system of claim 4, wherein the search for the orientation angle of the at least one mirror that minimizes the error measurement comprises:
  searching for the orientation angle of the at least one mirror that minimizes the error measurement using a Nelder-Mead search algorithm.

10. A method of tracking the sun with at least one heliostat mirror, a receiver, and a plurality of cameras in proximity to the receiver, the method comprising:
  generating a model of the sky, the model characterizing a level of light from of at least a portion of the sky;
  calculating coordinates of a portion of sky in a reflection of the at least one heliostat mirror;
  estimating, for each camera mounted in proximity to the receiver, a level of light of a portion of sky in a reflection of the at least one mirror based on the calculated coordinates and the model;
  determining, for each camera mounted in proximity to the receiver, a level of light of the portion of sky in the reflection of the at least one mirror based on the images from the plurality of cameras;
  generating an error measurement characterizing a difference between the level of light estimated from the model and the level of light determined from the images of the at least one mirror;
  searching for an orientation angle of the at least one mirror that minimizes the error measurement; and
  re-orienting the at least one heliostat mirror based on the orientation angle that minimizes the error measurement.

11. The method of claim 10, wherein the determined level of light is determined from one or more pixels associated with the portion of sky in the reflection of the at least one mirror visible in the images captured by the plurality of cameras mounted in proximity to the receiver.

12. The method of claim 11, wherein the level of light is determined based on an average or median brightness associated with the one or more pixels.

13. The method of claim 12, wherein the coordinates of the portion of sky in the reflection of the at least one mirror are calculated based on said one or more pixels.

14. The method of claim 13, wherein the plurality of cameras mounted in proximity to the receiver are mounted within ten meters of the receiver.

15. The method of claim 14, wherein the plurality of cameras mounted in proximity to the receiver are mounted within ten meters of a receiver aperture.

16. The method of claim 15, wherein the plurality of cameras comprise at least four cameras.

17. The method of claim 16, wherein the four cameras comprise a first camera above the receiver aperture, a second camera below the receiver aperture, a third camera to the left of the receiver aperture, and a fourth camera to the right of the receiver aperture.

18. The method of claim 13, wherein searching for the orientation angle of the at least one mirror that minimizes the error measurement comprises:
  searching for the orientation angle of the at least one mirror that minimizes the error measurement using a Nelder-Mead search algorithm.

19. A solar tracking system for orienting at least one heliostat mirror, the system comprising:
  a plurality of cameras mounted in proximity to a receiver, each camera configured to capture an image of the at least one mirror, each image including a reflection of a portion of the sky in the at least one mirror,
  a memory comprising a model of the sky, the model characterizing a light level of at least a portion of the sky; and
  a tracking controller configured to:
    a) for each camera mounted in proximity to the receiver, estimate a light level of a portion of sky in a reflection of the at least one mirror based on the model;
    b) for each camera mounted in proximity to the receiver, determine a light level of the portion of sky in the reflection of the at least one mirror based on the images from the plurality of cameras;
    c) generate an error measurement characterizing a difference between the light level estimated from the model and the light level determined from the images of the at least one mirror;

d) search for an orientation angle of the at least one mirror that minimizes the error measurement; and e) generate a command to re-orient the at least one mirror based on the orientation angle that minimizes the error measurement.

\* \* \* \* \*

UNITED STATES PATENT AND TRADEMARK OFFICE
CERTIFICATE OF CORRECTION

| | |
|---|---|
| PATENT NO. | : 11,554,035 B2 |
| APPLICATION NO. | : 17/329959 |
| DATED | : January 17, 2023 |
| INVENTOR(S) | : Alexander Sonn |

It is certified that error appears in the above-identified patent and that said Letters Patent is hereby corrected as shown below:

In the Specification

On Column 1, Line 8: Delete "11/017,561," and insert -- 16/594,937, --.

In the Claims

On Column 10, Line 51: In Claim 19, delete "mirror," and insert -- mirror; --.

Signed and Sealed this
Twenty-third Day of May, 2023

*Katherine Kelly Vidal*

Katherine Kelly Vidal
*Director of the United States Patent and Trademark Office*